US012599360B2

(12) United States Patent
Masters et al.

(10) Patent No.: US 12,599,360 B2
(45) Date of Patent: Apr. 14, 2026

(54) ULTRASONIC IMAGING ABLATION CATHETER SYSTEM AND METHOD

(71) Applicant: Boston Scientific Scimed, Inc., Maple Grove, MN (US)

(72) Inventors: Donald Masters, Sylmar, CA (US); Jesus Andres Lopez, Bloomington, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 535 days.

(21) Appl. No.: 18/049,214

(22) Filed: Oct. 24, 2022

(65) Prior Publication Data

US 2024/0130707 A1 Apr. 25, 2024
US 2024/0225591 A9 Jul. 11, 2024

(51) Int. Cl.
*A61B 8/12* (2006.01)
*A61B 18/14* (2006.01)
*A61B 8/00* (2006.01)

(52) U.S. Cl.
CPC ............ *A61B 8/12* (2013.01); *A61B 18/1492* (2013.01); *A61B 8/445* (2013.01)

(58) Field of Classification Search
CPC .................. A61B 5/287; A61B 5/6858; A61B 2018/00214; A61B 2018/00267; A61B 8/0883; A61B 8/12; A61B 8/114; A61B 8/4483; A61B 8/4488; A61B 18/1492; A61B 2018/1467
See application file for complete search history.

(56) References Cited

U.S. PATENT DOCUMENTS

| | | | |
|---|---|---|---|
| 5,628,313 A | 5/1997 | Webster, Jr. | |
| 5,870,351 A | 2/1999 | Ladabaum et al. | |
| 5,954,654 A | 9/1999 | Eaton et al. | |
| 6,277,077 B1 | 8/2001 | Brisken et al. | |

(Continued)

FOREIGN PATENT DOCUMENTS

| | | |
|---|---|---|
| WO | 2009/073753 A1 | 6/2009 |
| WO | 2023/091769 A1 | 5/2023 |

OTHER PUBLICATIONS

International Search Report and Written Opinion for PCT Application No. PCT/US2023/082324 mailed Jan. 21, 2025. 16 pages.
(Continued)

*Primary Examiner* — Eun Hwa Kim
(74) *Attorney, Agent, or Firm* — Nelson Mullins Riley & Scarborough LLP

(57) ABSTRACT

An integrated ultrasonic imaging and ablation system is disclosed. The system comprising an ablation catheter having a longitudinal axis, a proximal end, and a distal end. A micro-electromechanical (MEMS) based Piezoelectric Micromachined Ultrasonic Transducer (pMUT) or other ultrasound transducer disposed within the distal end of the ablation catheter. A catheter shaft is connected at one end to a handle assembly and at other end to the MEMS based pMUT array. A first carrier assembly is coupled to the catheter shaft and having a first array of electrodes coupled to a plurality of first carrier arms. A second carrier assembly is coupled to the catheter shaft and having a second array of electrodes coupled to a plurality of second carrier arms.

15 Claims, 7 Drawing Sheets

(56)                    References Cited

U.S. PATENT DOCUMENTS

| | | | |
|---|---|---|---|
| 6,547,788 B1 * | 4/2003 | Maguire ................. A61N 7/02 |
| | | | 606/49 |
| 9,454,954 B2 | 9/2016 | Hajati |
| 10,932,723 B2 | 3/2021 | Eliason et al. |
| 11,129,586 B1 * | 9/2021 | Moore ..................... A61B 8/02 |
| 2001/0047134 A1 | 11/2001 | Holdaway et al. |
| 2003/0199767 A1 | 10/2003 | Cespedes et al. |
| 2006/0083772 A1 | 4/2006 | Dewitt et al. |
| 2006/0235304 A1 | 10/2006 | Harhen et al. |
| 2007/0038111 A1 | 2/2007 | Rehrig et al. |
| 2007/0083194 A1 * | 4/2007 | Kunis ................ A61B 18/1492 |
| | | | 606/41 |
| 2007/0167764 A1 | 7/2007 | Hynynen |
| 2007/0185397 A1 | 8/2007 | Govari et al. |
| 2008/0091104 A1 | 4/2008 | Abraham |
| 2008/0208121 A1 | 8/2008 | Youssef et al. |
| 2009/0024040 A1 | 1/2009 | Cespedes |
| 2009/0088648 A1 | 4/2009 | Jaffe et al. |
| 2010/0152590 A1 | 6/2010 | Moore et al. |
| 2010/0168569 A1 | 7/2010 | Sliwa et al. |
| 2010/0168583 A1 | 7/2010 | Dausch et al. |
| 2010/0179424 A1 | 7/2010 | Warnking et al. |
| 2010/0305451 A1 | 12/2010 | Kim et al. |
| 2011/0015533 A1 | 1/2011 | Cox et al. |
| 2011/0028848 A1 | 2/2011 | Shaquer et al. |
| 2011/0257523 A1 | 10/2011 | Hastings et al. |
| 2012/0089028 A1 | 4/2012 | Hadani et al. |
| 2012/0253296 A1 | 10/2012 | Amano et al. |
| 2013/0053694 A1 | 2/2013 | Roschak et al. |
| 2013/0231735 A1 | 9/2013 | Deem et al. |
| 2013/0261467 A1 | 10/2013 | Dausch et al. |
| 2013/0267853 A1 | 10/2013 | Dausch et al. |
| 2013/0293065 A1 | 11/2013 | Hajati et al. |
| 2013/0294202 A1 | 11/2013 | Hajati |
| 2013/0303919 A1 * | 11/2013 | Corl ....................... A61B 8/445 |
| | | | 600/467 |
| 2014/0117812 A1 | 5/2014 | Hajati |
| 2014/0188103 A1 * | 7/2014 | Millett ............... A61B 18/1492 |
| | | | 607/113 |
| 2014/0236017 A1 | 8/2014 | Degertekin et al. |
| 2014/0276084 A1 | 9/2014 | Kemp |
| 2014/0276087 A1 | 9/2014 | Corl |
| 2015/0150497 A1 | 6/2015 | Goldchmit |
| 2015/0223757 A1 | 8/2015 | Werneth et al. |
| 2015/0265245 A1 | 9/2015 | Von et al. |
| 2015/0305708 A1 | 10/2015 | Stigall et al. |
| 2015/0366508 A1 | 12/2015 | Chou et al. |
| 2016/0029999 A1 | 2/2016 | Corl |
| 2016/0113633 A1 | 4/2016 | Hadjicostis |
| 2016/0199030 A1 | 7/2016 | Patil et al. |
| 2017/0209121 A1 | 7/2017 | Davis et al. |
| 2017/0252777 A1 | 9/2017 | Kidwell et al. |
| 2017/0290562 A1 | 10/2017 | Corl |
| 2018/0055477 A1 | 3/2018 | Eskuri |
| 2018/0064415 A1 | 3/2018 | Zhai et al. |
| 2018/0140278 A1 | 5/2018 | Bromberg et al. |
| 2018/0146948 A1 | 5/2018 | Chou et al. |
| 2018/0206819 A1 | 7/2018 | Saarinen et al. |

| | | | |
|---|---|---|---|
| 2018/0344283 A1 | 12/2018 | Rice et al. |
| 2019/0053783 A1 | 2/2019 | Stigall et al. |
| 2019/0069901 A1 | 3/2019 | Forbes |
| 2019/0105520 A1 | 4/2019 | Sverdlik et al. |
| 2019/0357879 A1 | 11/2019 | Corl |
| 2019/0374196 A1 | 12/2019 | Courtney et al. |
| 2020/0017906 A1 | 1/2020 | Lin et al. |
| 2020/0061340 A1 | 2/2020 | Mixter et al. |
| 2020/0155217 A1 | 5/2020 | Morneau et al. |
| 2020/0178788 A1 | 6/2020 | Waters et al. |
| 2020/0245977 A1 | 8/2020 | Hancock et al. |
| 2020/0330072 A1 | 10/2020 | Jacobs et al. |
| 2021/0000423 A1 * | 1/2021 | Werneth .............. A61B 5/0205 |
| 2021/0007711 A1 | 1/2021 | Van et al. |
| 2021/0030394 A1 | 2/2021 | Caswell et al. |
| 2021/0128106 A1 | 5/2021 | Salehi et al. |
| 2022/0048071 A1 | 2/2022 | Sudol |
| 2022/0168545 A1 | 6/2022 | Lopez et al. |
| 2022/0225960 A1 | 7/2022 | Cuscuna et al. |
| 2022/0346750 A1 | 11/2022 | Robinson et al. |
| 2022/0395255 A1 | 12/2022 | Ryan et al. |
| 2022/0401070 A1 | 12/2022 | Schaer et al. |
| 2023/0025475 A1 | 1/2023 | Graham et al. |
| 2023/0165559 A1 * | 6/2023 | Sutherland ........... A61B 8/4494 |
| | | | 600/459 |
| 2023/0377219 A1 | 11/2023 | Hennersperger et al. |
| 2024/0023933 A1 | 1/2024 | Masters et al. |

OTHER PUBLICATIONS

International Preliminary Report on Patentability received for PCT Patent Application No. PCT/US24/11835, mailed on Aug. 28, 2025, 12 pages.
International Preliminary Report on Patentability received for PCT Patent Application No. PCT/US24/11851, mailed on Aug. 28, 2025, 9 pages.
International Search Report and Written Opinion issued in PCT/US2023/0080430, mailed Apr. 11, 2024.
International Search Report and Written Opinion issued in PCT/US2024/011835, issued Jul. 9, 2024.
International Search Report and Written Opinion issued in PCT/US2024/016370, mailed Jul. 18, 2024.
International Search Report and Written Opinion issued PCT/US2024/011851, issued on May 17, 2024.
International Search Report and Written Opinion received for PCT Patent Application No. PCT/US23/78696, mailed on Mar. 4, 2024, 6 pages.
Piezoelectric Micromachined Ultrasonic Transducers (PMUT) (Year: 2024).
Richardson et al., "Physiological Implications of Myocardial Scar Structure", 2015, Comprehensive Physiology, vol. 5 Issue 4 (Year: 2015).
Seif et al. "Emergency department diagnosis of infective endocarditis using bedside emergency ultrasound", 2013, Critical Ultrasound Journal, 5:1 (Year: 2013).
Written Opinion and International Search Report issued in PCT/US2024/011842, issued May 17, 2024, 9 pages.

* cited by examiner

300

302

308 — Display

310 — Image Processor

312 — Receive Beamformer    Transmit Beamformer — 314

316 — Dongle

306

304 — Ablation Catheter

304

302

402

306

404

406

ULTRASONIC IMAGING ABLATION CATHETER SYSTEM AND METHOD

FIELD OF THE DISCLOSURE

The present disclosure relates generally to the field of ablation and ablation catheters. More particularly, embodiments relate to ablation catheters incorporating an ultrasound transducer for imaging utilizing a distal piezoelectric micromachined transducer for transmitting and receiving acoustic pulse information.

BACKGROUND OF THE DISCLOSURE

Use of catheter-based structural and electrophysiological procedures have recently expanded to more complex scenarios, in which an accurate definition of variable individual cardiac anatomy is a key to obtain optimal results. In electrophysiology procedures, imaging allows integration of real-time images with ablation. Imaging integration allows a real-time assessment of cardiac anatomy during interventional procedures and guides catheter manipulation in relation to the different anatomic structures.

Catheter ablation is an alternative treatment option that is more effective than antiarrhythmic medications. Pulmonary vein isolation (PVI), which involves electrically isolating the pulmonary veins (PV) from the left atrium, remains the cornerstone of Atrial Fibrillation (AF) ablation. Typically, modern ablative technologies which may improve the efficacy, safety, and efficiency of ablation for persistent AF. These techniques include high-power short-duration (HPSD) radio frequency (RF) delivery, single-shot RF balloons, advances in cryoablation, and electroporation. Further, current technology requires the use of ablation catheter and an Intracardiac Echocardiography (ICE) imaging catheter. ICE has applications for structural heart imaging of the left atrial appendage (LAA), to aid in septal defect closures and visualizing the fossa ovalis and plays a role in transcatheter valve replacement. It also is used in EP procedures for ablation catheter guidance. ICE confirms the exact location of the catheter tip to aid with more accurate ablations. ICE also can help with safety monitoring of the pericardial space for tamponade or pericardial effusion caused in rare cases by either the transeptal puncture or the ablation. ICE is expected to become increasingly important to better guide an increasing number of transcatheter ablation procedures. Once transcatheter aortic and mitral valve heart valve replacement and LAA occlusion devices gain U.S. Food and Drug Administration (FDA) clearance, ICE is expected to see increased use for the accurate deployment of these devices.

Further, the AF is one of the most widespread and sustained cardiac arrhythmias and it affects more than 30 million people worldwide. While prevalence in developed nations tends to be small, nearly 1%-4%. The AF is steadily increasing, and it is well known that the AF is associated with an increased risk of all-cause mortality, heart failure, thromboembolism, and dementia. Further, the AF refers to a type of cardiac arrhythmia where there is disorganized electrical conduction in the atria causing rapid uncoordinated contractions that result in ineffective pumping of blood into the ventricle and a lack of synchrony. During AF, the atrioventricular node receives electrical impulses from numerous locations throughout the atria instead of only from the sinus node. This overwhelms the atrioventricular node into producing an irregular and rapid heartbeat. As a result, blood pools in the atria that increases a risk for blood clot formation. The major risk factors for atrial fibrillation include age, coronary artery disease, rheumatic heart disease, hypertension, diabetes, and thyrotoxicosis. The AF affects 7% of the population over age 65.

Moreover, the AF treatment options are limited. Lifestyle change only assists individuals with lifestyle related AF. Medication therapy assists only in the management of AF symptoms, may present side effects more dangerous than atrial fibrillation, and fail to cure AF. Electrical cardioversion often restores sinus rhythm but has a high recurrence rate. In addition, if there is a blood clot in the atria, cardioversion may cause the clot to leave the heart and travel to the brain or to some other part of the body, which may lead to stroke. Therefore, there is a need for an improved ultrasonic imaging and ablation system.

SUMMARY OF THE DISCLOSURE

By way of introduction, the preferred embodiments described below include an easy-to-use integrated ultrasonic imaging and ablation system is disclosed. The integrated ultrasonic imaging and ablation system comprises an ablation catheter having a longitudinal axis, a proximal end, and a distal end. Further, an ultrasonic transducer array is disposed within the distal end of the ablation catheter. The ultrasonic transducer array comprises a plurality of transducer array elements arranged on a substrate. It can be noted that the plurality of transducer array elements corresponds to a micro-electromechanical (MEMS) based Piezoelectric Micromachined Ultrasonic Transducer (pMUT) or other type of transducer. Further, the integrated ultrasonic imaging and ablation system comprises a catheter shaft connected at one end to a handle assembly and at other end to the ultrasonic transducer array. Further, the integrated ultrasonic imaging and ablation system comprises a first carrier assembly coupled to the catheter shaft and having a first array of electrodes coupled to a plurality of first carrier arms. Further, the integrated ultrasonic imaging and ablation system comprises a second carrier assembly coupled to the catheter shaft and having a second array of electrodes coupled to a plurality of second carrier arms.

According to another aspect of the invention, an integrated ultrasound imaging and ablation system is disclosed. The integrated ultrasound imaging and ablation system comprises an ablation catheter having a longitudinal axis, a proximal end, and a distal end. Further, the integrated ultrasound imaging and ablation system comprises a MEMS based pMUT array disposed within the distal end of the ablation catheter. The MEMS based pMUT array comprises a substrate and a plurality of MEMS based pMUT array elements arranged on the substrate. Further, the integrated ultrasound imaging and ablation system an electronic flex cable connected at one end to a handle assembly and at other end to the MEMS based pMUT array. The electronic flex cable is in communication with at least one signal trace, and is configured to: direct each of the plurality of MEMS based pMUT array elements, via the at least one signal trace, to transmit and receive, with respect to heart, ultrasound beams; receive at least one signal from the plurality of MEMS based pMUT array elements based on transmitting and receiving at least one ultrasound beam of the ultrasound beams; and construct at least one image of at least a portion of the heart based on the at least one signal.

According to another aspect of the invention, an ablation catheter for an operator to treat a patient with an arrhythmia is disclosed. The catheter includes an elongate, flexible tubular body member have a proximal end, a distal end, and a lumen between. The catheter further includes a control shaft, coaxially disposed and slidingly received with the lumen of the tubular body member. A flexible carrier assembly is attached to the end of the control shaft and includes at least one imaging, ablation and/or mapping elements. Retraction of the control shaft causes the carrier assembly to transition from a compact, near linear configuration, to a helix or partial helix.

In a preferred embodiment, the catheter includes an ultrasound array for directing ultrasound energy in a circular pattern toward tissue. In a preferred embodiment, the catheter includes an ultrasound array for directing ultrasound energy in a controlled direction toward tissue.

According to another aspect of the invention, a medical device is disclosed. The medical device comprises a catheter shaft, a first carrier assembly and a second carrier assembly. The first carrier assembly coupled to the catheter shaft and having a first radially expandable array of electrodes coupled to a plurality of first carrier arms. The second carrier assembly rotatably coupled to the catheter shaft and having a second radially expandable array of electrodes coupled to a plurality of second carrier arms, the second carrier assembly rotatable about the first carrier assembly.

In a preferred embodiment, the first carrier assembly and the second carrier assembly can be withdrawn into a location within the tubular body member. In another preferred embodiment, the ablation catheter includes at least two carrier assemblies that can be transitioned between a compact, near linear configuration to a helix or partial helix. In yet another preferred embodiment, the ablation catheter can be placed over a guidewire or includes an integral guidewire tip.

According to yet another aspect of the invention, an ablation catheter for an operator to treat a patient with an arrhythmia is disclosed. The ablation catheter includes an elongate, flexible tubular body member have a proximal end, a distal end, and a lumen there between. The ablation catheter further includes a flexible carrier assembly comprising an inflatable balloon with mounted or imaging, embedded ablation and/or mapping elements.

One such example of a minimally invasive therapy involves the treatment of cardiac arrhythmias or irregular heartbeats in which physicians employ specialized cardiac assessment and treatment devices, such as mapping catheters and ablation catheters, to gain access to, diagnose, and treat interior regions of a patient's body.

Such devices may include energized electrodes or other ablation assemblies to create lesions or other anatomical effects that disrupt or block electrical pathways through the targeted tissue.

BRIEF DESCRIPTION OF THE DRAWINGS

The accompanying drawings illustrate various embodiments of systems, methods, and embodiments of various aspects of the disclosure. Any person of ordinary skill in the art will appreciate that the illustrated element boundaries (e.g., boxes, groups of boxes, or other shapes) in the figures represent one example of the various boundaries representative of the disclosed invention. It may be that in some examples one element may be designed as multiple elements or that multiple elements may be designed as one element. In other examples, an element shown as an internal component of one element may be implemented as an external component in another and vice versa. Furthermore, elements may not be drawn to scale. Non-limiting and non-exhaustive descriptions of the present disclosure are described with reference to the following drawings. The components in the figures are not necessarily to scale, emphasis instead being placed upon the illustrated principles.

Various embodiments will hereinafter be described in accordance with the appended drawings, which are provided to illustrate and not to limit the scope of the disclosure in any manner, wherein similar designations denote similar elements, and in which.

DETAILED DESCRIPTION

The components of the embodiments as generally described and illustrated in the figures herein can be arranged and designed in a wide variety of different configurations. Thus, the following more detailed description of various embodiments, as represented in the figures, is not intended to limit the scope of the present disclosure but is merely representative of various embodiments. While various aspects of the embodiments are presented in drawings, the drawings are not necessarily drawn to scale unless specifically indicated.

Some embodiments of this disclosure, illustrating all its features, will now be discussed in detail. The words "comprising," "having," "containing," and "including," and other forms thereof, are intended to be equivalent in meaning and be open-ended in that an item or items following any one of these words is not meant to be an exhaustive listing of such item or items or meant to be limited to only the listed item or items.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred systems, and methods are now described. The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Embodiments of the present disclosure will be described more fully hereinafter with reference to the accompanying drawings in which like numerals represent like elements throughout the several figures, and in which example embodiments are shown. Embodiments of the present disclosure may, however, be embodied in alternative forms and should not be construed as being limited to the embodiments set forth herein. The examples set forth herein are non-limiting examples and are merely examples among other possible examples.

Figure 1:
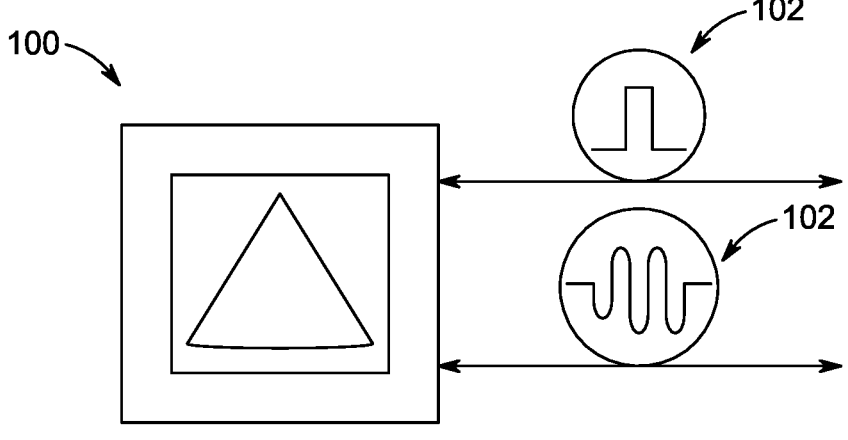
FIGS. 1 and 2 illustrate a prior art imaging system, for acquiring two-dimensional image information.
Figure 2:
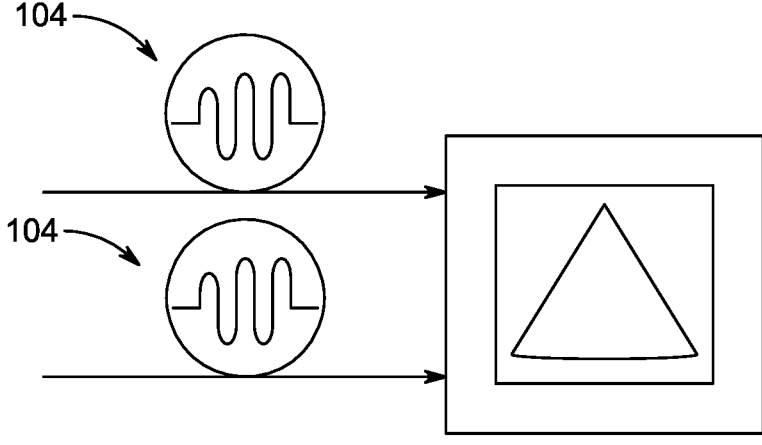

FIGS. 1 and 2 illustrate a prior art imaging system 100. The imaging system 100 provides an ultrasound transmit pulse 102 and an ultrasound receive path 104, for connection to an ultrasonic transducer (not shown). The ultrasound transmit pulse 102 may transmit ultrasound signals from the imaging system 100 towards an object such as heart of a patient. Further, the ultrasound receive path 104 may create a waveform based at least on the ultrasound signals. Thereafter, the imaging system 100 may convert the received ultrasound signals or ultrasound information to a two-dimensional (2D) image of the object or a portion of the object.

Figure 3:
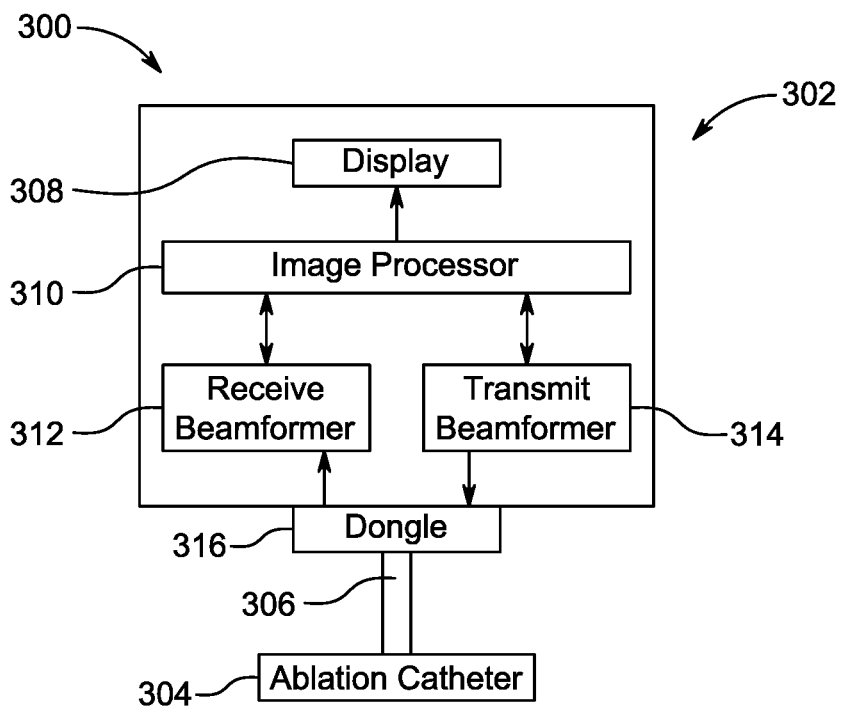
FIG. 3 illustrates a schematic diagram of an ultrasonic imaging system, according to an embodiment of the present disclosure.

FIG. 3 illustrates a schematic diagram of an ultrasonic imaging system 300, according to an embodiment of the present disclosure.

In one embodiment, the ultrasonic imaging system 300 may utilize a microelectromechanical (MEMS) transducer array defined as piezoelectric micro-machined ultrasound transducer (pMUT) or other types of MEMS transducers, interconnected using matched flexible circuits. It can be noted that the use of the high-density flexible circuits may enable highly repeatable and stable transmission and return signals. Further, the high-density flexible circuit transmission lines may transmit electrical energy from one end to another distal end of the ultrasonic imaging system 300.

The ultrasonic imaging system 300 may comprise an imaging device 302 linked to an ablation catheter 304 via a communication channel 306. The imaging device 302 may comprise a display 308, an image processor 310, a receive beamformer 312, a transmit beamformer 314 and a dongle 316. The ablation catheter 304 may be disposed within a chamber of a heart of a patient and the imaging device 302 may receive at least one signal from the ablation catheter 304. The at least one signal may be communicated from the ablation catheter 304 to the imaging device 302 via an electronic flex cable (not shown) connected to the dongle 316.

The image processor 310 may be configured to generate a two-dimensional (2D) image according to data received from the ablation catheter 304. In one embodiment, the image processor 310 may be configured to receive a focused signal from the receive beamformer 312. The image processor 310 may render the data to construct an image or sequence of images. In one embodiment, the image may be three-dimensional (3D) representation, such as a two-dimensional image rendered from a user or a processor selected viewing direction. In one embodiment, the image processor 310 may be a detector, filter, processor, application-specific integrated circuit, field-programmable gate array, digital signal processor, control processor, scan converter, three-dimensional image processor, graphics processing unit, analog circuit, digital circuit, or combinations thereof. The image processor 310 may receive beamformed data and may generate images, to display on the display 308. It can be noted that the generated images are associated with a two-dimensional (2D) scan. Alternatively, the generated images may be three-dimensional (3D) representations.

The image processor 310 may be programmed for hardware accelerated two-dimensional re-constructions. The image processor 310 may store processed data of the at least one signal and a sequence of images in a memory. In one embodiment, the memory may be a non-transitory computer-readable storage media. The instructions for implementing the processes, methods and/or techniques discussed herein are provided on the computer-readable storage media or memories, such as a cache, buffer, RAM, removable media, hard drive, or other computer-readable storage media. Non-transitory computer-readable storage media include various types of volatile and non-volatile storage media. The functions, acts, or tasks illustrated in the figures or described herein are executed in response to one or more sets of instructions stored in or on a computer readable storage media. The functions, acts, or tasks are independent of the particular type of instruction sets, storage media, processor, or processing strategy and may be performed by software, hardware, integrated circuits, firmware, micro code, and the like, operating alone or in combination.

Figure 6:
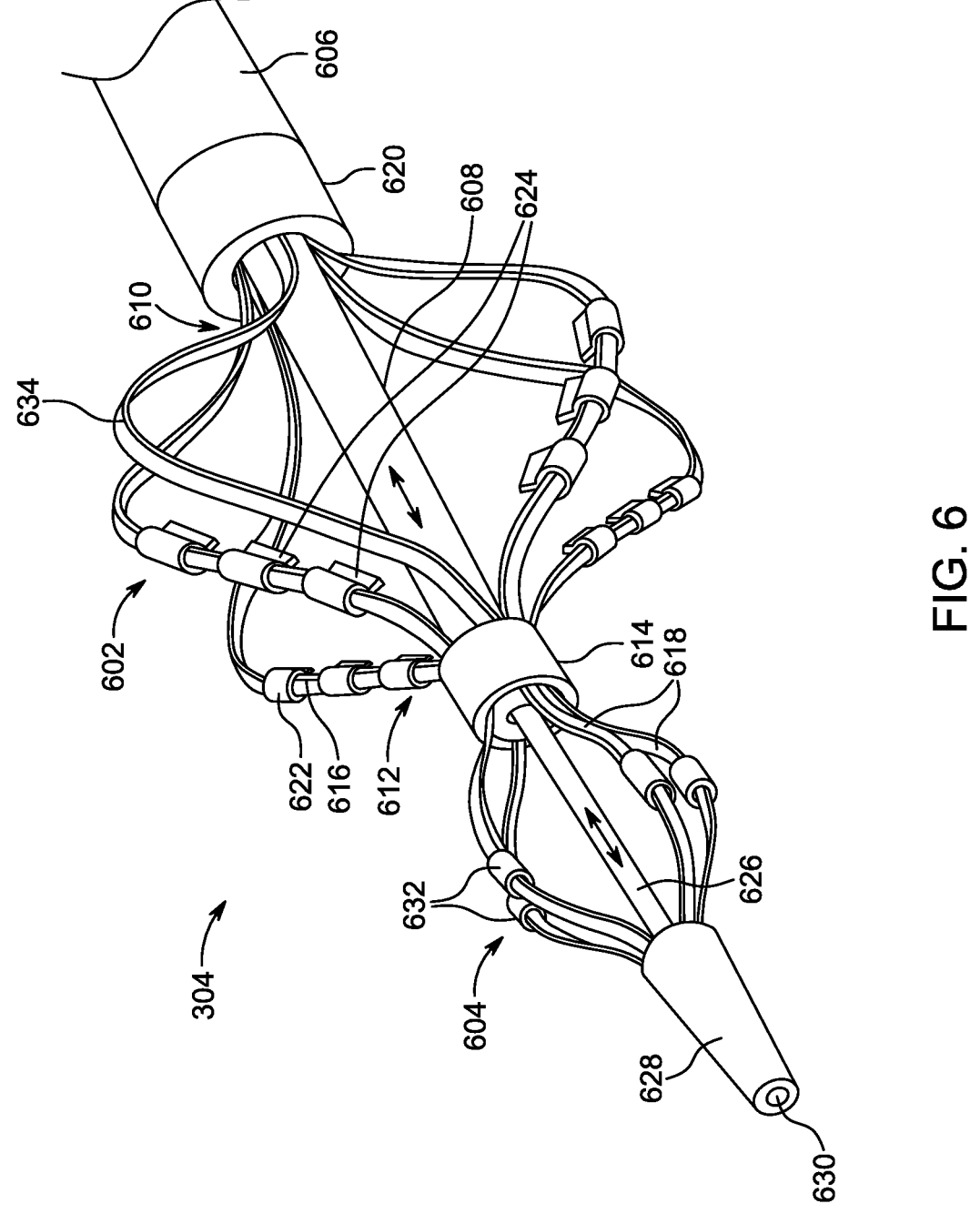
FIG. 6 illustrates a perspective view of the distal end of the ablation catheter, according to an embodiment of the present disclosure.

The ablation catheter 304 may be in electronic communication with the imaging device 302 for transmission and receiving of ultrasound signals to and from an arterial wall of a vascular system. In one embodiment, the ablation catheter 304 may be configured to visualize standard echocardiography views of the heart, such as in a standard version, a right atrium may be visualized. The ablation catheter 304 may be employed in transseptal catheterization for several percutaneous interventions, including left heart catheter ablation, atrial septal defect closure for effective alternative to surgical intervention. In one embodiment, the ablation catheter 304 may comprise a body having a longitudinal axis, a proximal end, a distal end, a handle assembly, a catheter shaft, an electronic flex cable, and a distal tip, as shown in FIG. 6.

Figure 4:
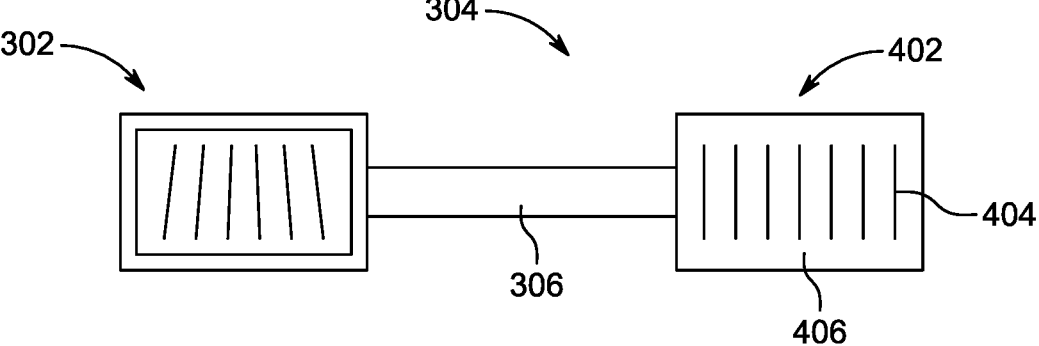
FIG. 4 illustrates a multi-channel electronic communication between an imaging device and an ablation catheter, according to an embodiment of the present disclosure.

Referring to FIG. 4, a multi-channel electronic communication between the ultrasonic imaging device 302 and the ablation catheter 304 is disclosed, according to an embodiment of the present disclosure.

The ablation catheter 304 may comprise a MEMS based pMUT array 402 coupled to the imaging device 302 via the catheter shaft (not shown) and the dongle 316. The dongle 316 may be referred as a communication channel connected to the catheter shaft.

The MEMS based pMUT array 402 may comprise a plurality of pMUT array elements 404 arranged on a substrate 406. Further, each of the plurality of pMUT array elements 404 may provide a wide bandwidth of an individual focused beam. The MEMS based pMUT array 402 may be coupled to the ultrasonic imaging device 302 using the dongle 316, as described earlier. The MEMS based pMUT array 402 disposed within the distal end of the ablation catheter 304 may transmit the at least one signal via the electronic flex cable inside the catheter shaft to the imaging device 302. The at least one signal may be the acoustic echo transmitted from the MEMS based pMUT array 402. It can be noted that the acoustic echo of acoustic energy may be received from a face of the MEMS based pMUT array 402 and received at the image processor 310.

Further, the ablation catheter 304 may comprise a plurality of steering cables (not shown) configured to direct each of the plurality of pMUT array elements 404, via the at least one signal trace, to transmit and receive, ultrasound beams. The ultrasound beams may have a bandwidth including a predetermined fundamental mode vibration of each of the plurality of pMUT array elements 404, such that a single array element can transmit and receive multiple fundamental mode vibrations simultaneously. It can be noted that the plurality of pMUT array elements 404 may transmit and receive the ultrasound beams with respect to the heart or at least a portion of the heart. Further, the electronic flex cable inside the catheter shaft may be configured to receive at least one signal from the plurality of pMUT array elements 404 based on transmitting and receiving at least one ultrasound beam of the ultrasound beams. The imaging device 302 may be further configured to construct at least one image of at least the portion of the heart based on the at least one signal. It can be noted that the electronic flex cable may be configured to the transmit beamformer 314 and the receive beamformer 312 to display a two-dimensional (2D) image information of the heart or the at least portion of the heart.

In one embodiment, the plurality of pMUT array elements 404 may correspond to MEMS based pMUTs. The catheter shaft may be connected to the handle assembly 324 at one end and to the MEMS based pMUT array 402 at other end. The electronic flex cable inside the catheter shaft may be in communication with the at least one signal trace. It can be noted that the electronic flex cable may be further communicate to the transmit beamformer 314 and the receive beamformer 312, via the dongle 316 to display a two-dimensional (2D) image information of the heart to be scanned.

Figure 5:
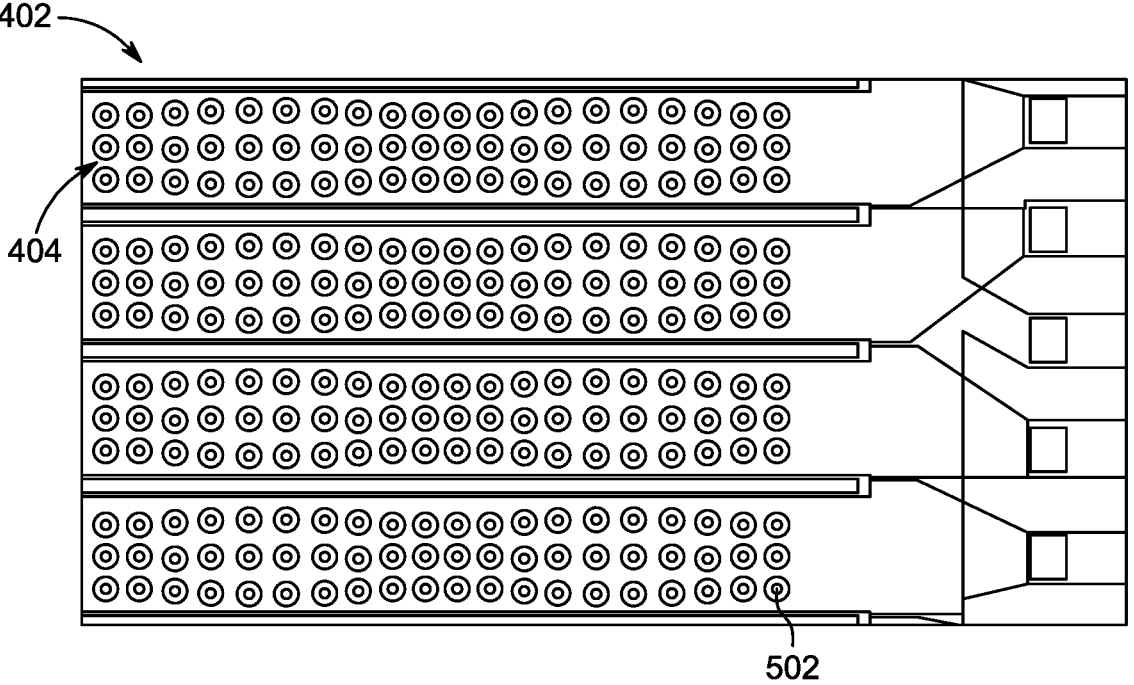
FIG. 5 illustrates a sectional view of a distal end of the ablation catheter with a plurality of transducer array elements, according to an embodiment of the present disclosure.

Referring to FIG. 5, a sectional view of a distal end of the ablation catheter 304 with a plurality of transducer array elements 402 is disclosed, according to an embodiment of the present disclosure.

The MEMS based pMUT array 402 may comprise the plurality of pMUT array elements 404, arranged towards the distal end of the ablation catheter 304. The distal end of the ablation catheter may be provided with the MEMS based pMUT array 402 having the plurality of pMUT array elements 404. Further, each of the plurality of pMUT array elements 404 may have a plurality of individual transducer cells 502 arranged in a manner to provide a wide bandwidth of the individual focused beam. In one embodiment, the MEMS based pMUT array 402 may be constructed from a pMUT array containing individual elements of different diameters. In one embodiment, to achieve wider bandwidth with pMUT arrays, multiple diameters of pMUT cells may be integrated into one element. It can be noted that by arranging pre-shaped pMUTs with different diameters, a broader bandwidth can be realized through the complex interaction between the individual pMUT elements. In one embodiment, the pMUT cells of multiple diameters may achieve a bandwidth of greater than 55%. For example, in 3 elements, there are 5 different dome diameters, and each array is of a different size, such as 300 μm.

Figure 7:
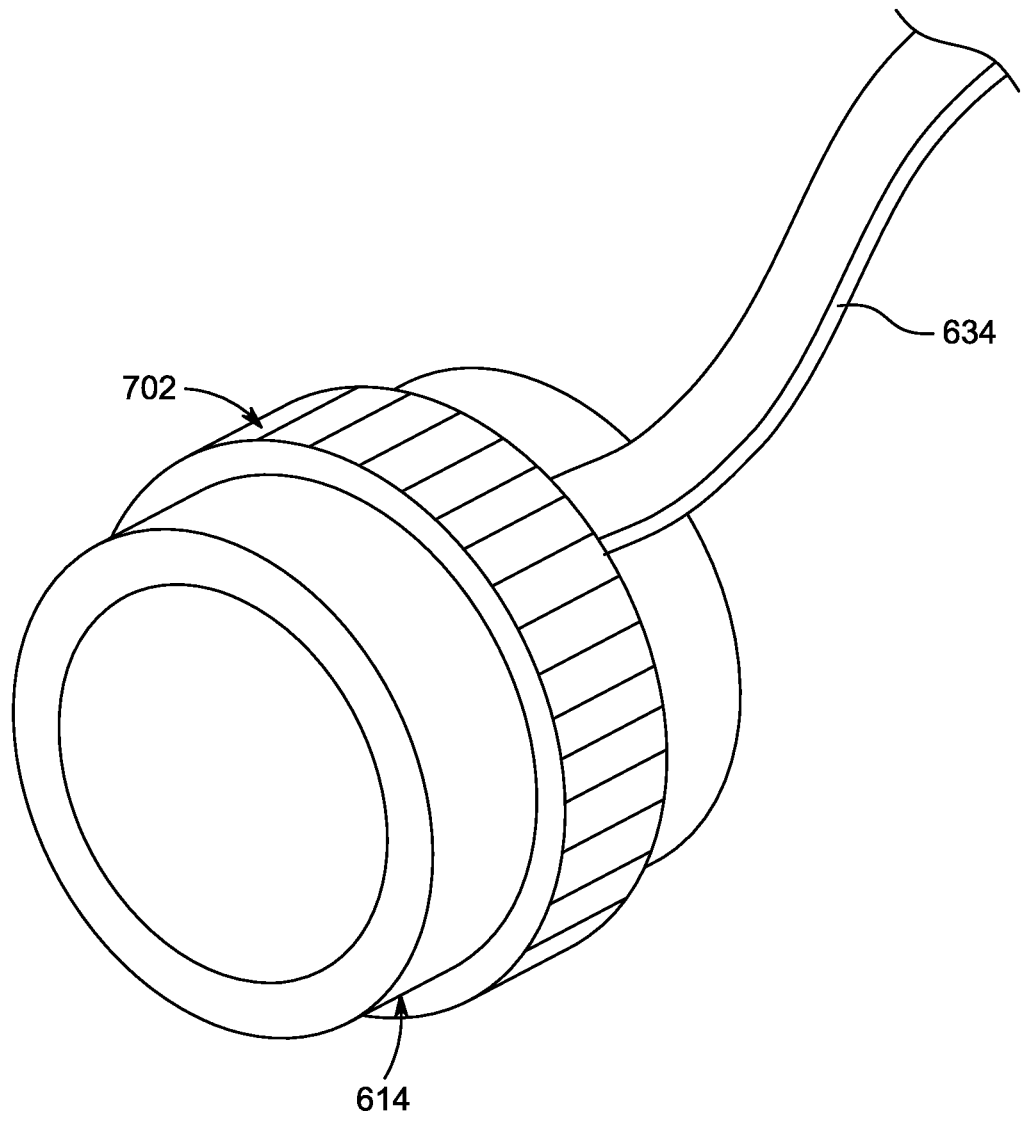
FIG. 7 illustrates a plurality of circular arrays arranged in a cylindrical fashion, according to an embodiment of the present disclosure.
Figure 8:
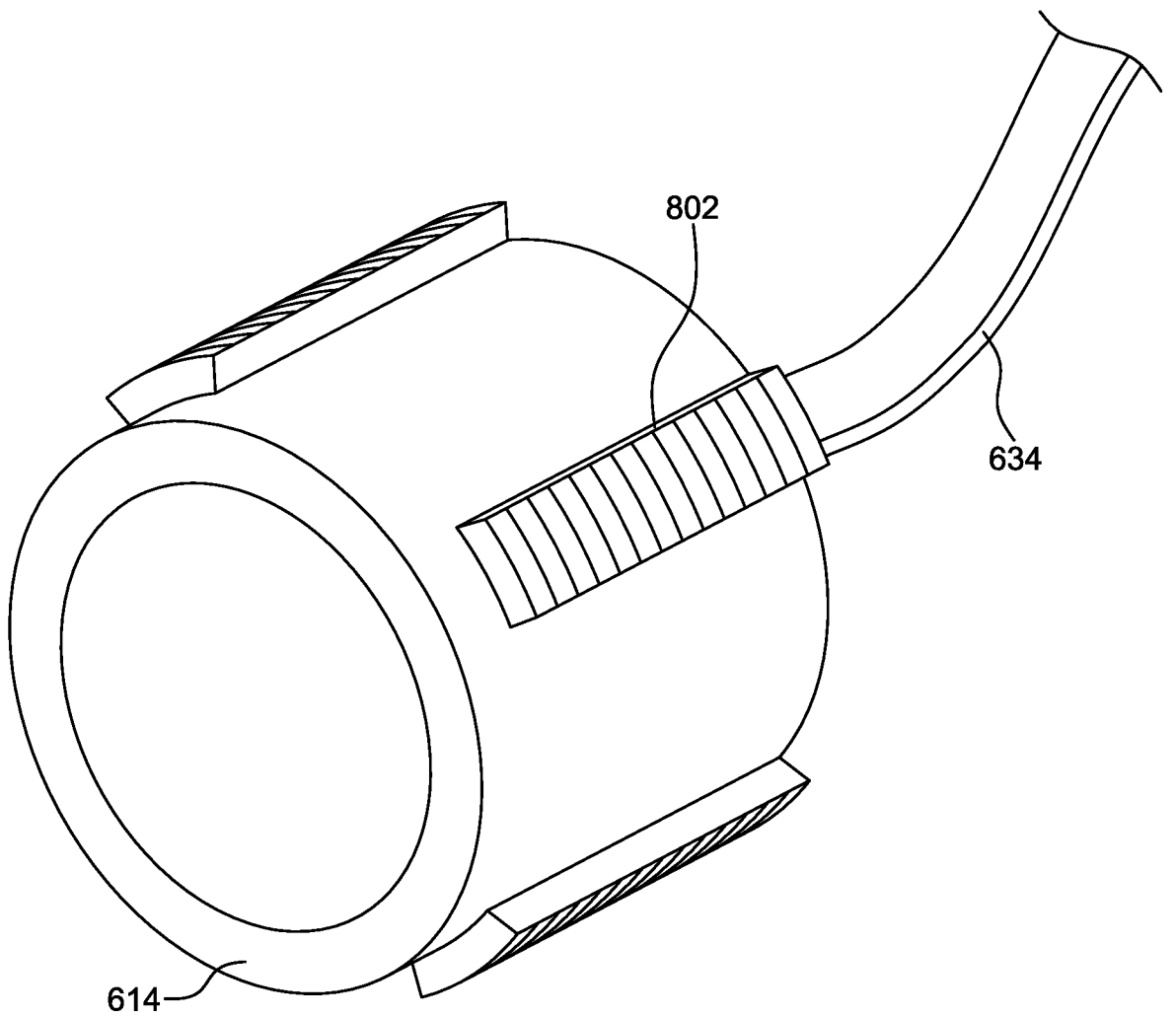
FIG. 8 illustrates a plurality of linear arrays arranged in a cylindrical fashion, according to an embodiment of the present disclosure.

Further, the MEMS based pMUT array 402 may correspond to pMUT and the plurality of pMUT array elements 404 may correspond to a plurality of pMUT elements. In one embodiment, the plurality of pMUT elements may be directed to transmit and receive, the ultrasound beams having the bandwidth including the predetermined fundamental mode vibration of each of the plurality of pMUT elements, such that a single pMUT element can transmit and receive multiple fundamental mode vibrations simultaneously. Further, the electronic flex cable inside the catheter shaft receives the at least one signal from the plurality of pMUT elements. It can be noted that the at least one signal may correspond to the at least one ultrasound beam. The at least one signal may be transmitted to the ultrasonic imaging device 302 for further processing in the image processor 310. The image processor 310 may construct the at least one image of the heart. It can be noted that the plurality of pMUT elements may be used to create the individual focused beam. In one embodiment the pMUT elements are arranged in a linear fashion. In a second embodiment the pMUT in arranged in cylinder fashion, as shown in FIGS. 7-8.

Referring to FIG. 6, a perspective view of the distal end of the ablation catheter 304 is disclosed. The ablation catheter 304 may comprise a proximal energy delivering carrier assembly 602 and a distal mapping carrier assembly 604.

The proximal energy delivering carrier assembly 602 and the distal mapping carrier assembly 604 may be disposed serially along a single axis, with each of the proximal energy delivering carrier assembly 602 and the distal mapping carrier assembly 604 in an umbrella tip configuration. Further, the ablation catheter 304 includes an elongate tube as an outer shaft 606, preferably constructed of Pebax material and approximately 6-8 Frin diameter. The outer shaft 606 slidingly receives a first control shaft 608. The first control shaft 608 is attached on a distal portion to the proximal energy delivering carrier assembly 602. It can be noted that the proximal energy delivering carrier assembly 602 comprises multiple carrier arms and ablation elements configured to deliver energy. The proximal energy delivering carrier assembly 602 may have a first end 610 and a second end 612. The first end 610 of the proximal energy delivering carrier assembly 602 is attached to a control on the proximal end of the ablation catheter 304 configured to allow an operator to precisely advance and retract the proximal energy delivering carrier assembly 602.

The proximal energy delivering carrier assembly 602 may comprise a first ring 614 on the second end 612. The first ring 614 fixedly attaches one end of each distal carrier arm segment 616 to the proximal energy delivering carrier assembly 602. Each distal carrier arm segment 616 is pivotally attached on an opposite end to one end of a proximal carrier arm segment 618. Further, an opposite end of each proximal carrier arm segment 618 is fixedly attached to the first end 610 of the proximal energy delivering carrier assembly 602 towards the outer shaft 606 via a second ring 620.

In one embodiment, the distal carrier arm segments 616 and the proximal carrier arm segments 618 are constructed of a flexible material. In another embodiment, the distal carrier arm segments 616 and the proximal carrier arm segments 618 may be made from Nitinol. It can be noted that Nitinol is resiliently biased in a straight or umbrella tip configuration. Further, advancement and retraction of the first control shaft 608 changes the diameter of the proximal energy delivering carrier assembly 602, including a fully compacted (minimal diameter) radial state when the first control shaft is fully advanced, and a maximum diameter state when first control shaft 608 is fully retracted.

Further, the ablation catheter 304 may comprise ablation and mapping elements 622 fixedly mounted to each of the distal carrier arm segment 616. The ablation and mapping elements 622 are configured to deliver energy to tissue to create lesions for disrupting aberrant electrical pathways in the tissue. Further, the ablation and mapping elements 622 may comprise fins 624 configured to reside in a flow of blood during energy delivery and provide sinking of heat into the circulating blood. In one embodiment, the ablation and mapping elements 622 are configured to deliver monopolar, bipolar or a combination of monopolar and bipolar RF energy as has been described above. The ablation and mapping elements 622 comprise integral temperature sensors, such as a thermocouple welded to an internal portion of each of the ablation and mapping elements 622. In another embodiment, the ablation and mapping elements 622 and integral temperature or other sensors, are attached to wires (not shown) which travel proximally to the proximal end of the ablation catheter 304 for attachment to an energy delivery unit, a mapping unit, and/or another electronic device for sending or receiving signals and/or power.

Further, the first control shaft 608 slidingly receives a second control shaft 626. The second control shaft 626 is attached on a distal portion to distal mapping carrier assembly 604. The distal mapping carrier assembly 604 may comprise multiple carrier arms and ablation elements configured to map electrical activity. A proximal end of the second control shaft 626 is attached to a control on the proximal end of ablation catheter 304 and configured to allow an operator to precisely advance and retract the second control shaft 626. Further, the second control shaft 626 comprises a distal tip 628 towards a distal end. The distal tip 628 may be fixedly attached one end of each distal carrier arm segment 616 to the second control shaft 626.

In one embodiment, the distal tip 628 may be preferably constructed of a soft or flexible material, such as, a soft plastic or an elastomer which is atraumatic to tissue and is preferably radiopaque, such as a Pebax material doped with Barium Sulfate. It can be noted that the distal tip 628 is constructed to help navigation into and stabilization within a pulmonary vein.

The distal tip 628 may comprise a guidewire lumen 630 is in fluid communication with an internal lumen (not shown) of the second control shaft 626. The guidewire lumen 630 may travel to and exit a proximal portion of ablation catheter 304, such that ablation of the proximal end of the ablation catheter 304 for attachment to an imaging engine, mapping unit, an energy delivery unit, and/or another electronic device for sending or receiving signals and/or power. It can be noted that the ablation catheter 304 can be percutaneously inserted into the vasculature of a patient over a guidewire.

Further, each distal carrier arm segment 616 is pivotally attached on the opposite end to one end of the proximal carrier arm segment 618. Further, each opposite end of the proximal carrier arm segment 618 is fixedly attached to the distal end of the first control shaft 608 via the first ring 614. In one embodiment, the distal carrier arm segments 616 and the proximal carrier arm segments 618 are constructed of a flexible material. Further, an advancement and retraction of the second control shaft 626 changes the diameter of the distal mapping carrier assembly 604, including a fully compacted (minimum diameter) radial state when the second control shaft 626 is fully advanced, and a maximum diameter state when the second control shaft 626 is fully retracted.

Further, the distal mapping carrier assembly 604 may comprise ablation elements, mapping electrodes 632 fixedly mounted to the distal carrier arm segments 616. Further, the ablation elements, and the mapping electrodes 632 are configured to map electrical activity present in tissue to target areas for creating lesions and/or otherwise assess a patient condition. In one embodiment, the mapping electrodes 632 are constructed of a conductive material, such as platinum or a combination of platinum and iridium. Further, the mapping electrodes 632 may comprise integral temperature sensors, such as a thermos couple welded to an internal portion of the mapping electrode 632. In another embodiment, the mapping electrode 632 and integral temperature or other sensors, are attached to wires (not shown) which travel proximally to the proximal portion of the ablation catheter 304 for attachment to an imaging engine, mapping unit, an energy delivery unit, and/or another electronic device for sending or receiving signals and/or power.

Further, an electronic flex cable 634 may be mounted between the first end 610 and the second end 612 of the proximal energy delivering carrier assembly 602. The electronic flex cable 634 at one end, is inserted inside the second ring 620 towards the second end 612 of the proximal energy delivering carrier assembly 602. Further, the electronic flex cable 634 at other end, advances inside the first ring 614 towards the first end 610 of the proximal energy delivering carrier assembly 602. The electronic flex cable 634 may have same length as that of the proximal carrier arm segment 618. Further, the first ring 614 may be mounted with MEMS based pMUT transducers configured to image the heart walls, as shown in FIGS. 7-8.

In one embodiment, the first ring 614 having a circular array 702 arranged in a cylindrical fashion is shown in FIG. 7. The electronic flex cable 634 may be connected to the circular array 702. In one embodiment, the circular array 702 correspond to the pMUT elements.

In another embodiment, the first ring 614 having a plurality of linear arrays 802 arranged in linear fashion is shown in FIG. 8. In one embodiment, the circular array 702 and the plurality of linear arrays 802 may be arrays of ablation elements, preferably geometrically adjustable electrode arrays, and may be configured in a wide variety of ways and patterns. In another embodiment, the circular array 702 and the plurality of linear arrays 802 provide electrical energy, such as radiofrequency (RF) energy, in monopolar (unipolar), bipolar or combined monopolar-bipolar fashion, as well as methods for treating conditions (e.g., atrial fibrillation, supra ventricular tachycardia, atrial tachycardia, ventricular tachycardia, ventricular fibrillation, and the like). Further, multiple types of ablation catheters may be employed for different minimally invasive procedures, such as, atrioventricular (AV) node ablation which is a treatment for an irregularly fast and disorganized heartbeat called atrial fibrillation, cryoablation in which an extremely cold liquid or an instrument called a cryoprobe is used to freeze and eliminate abnormal tissue, and an epicardial ablation in which a regular heart rhythm is restored, by creating tiny scars on outside of the heart to block faulty electrical signals that cause the heart to beat too fast.

Figure 9:
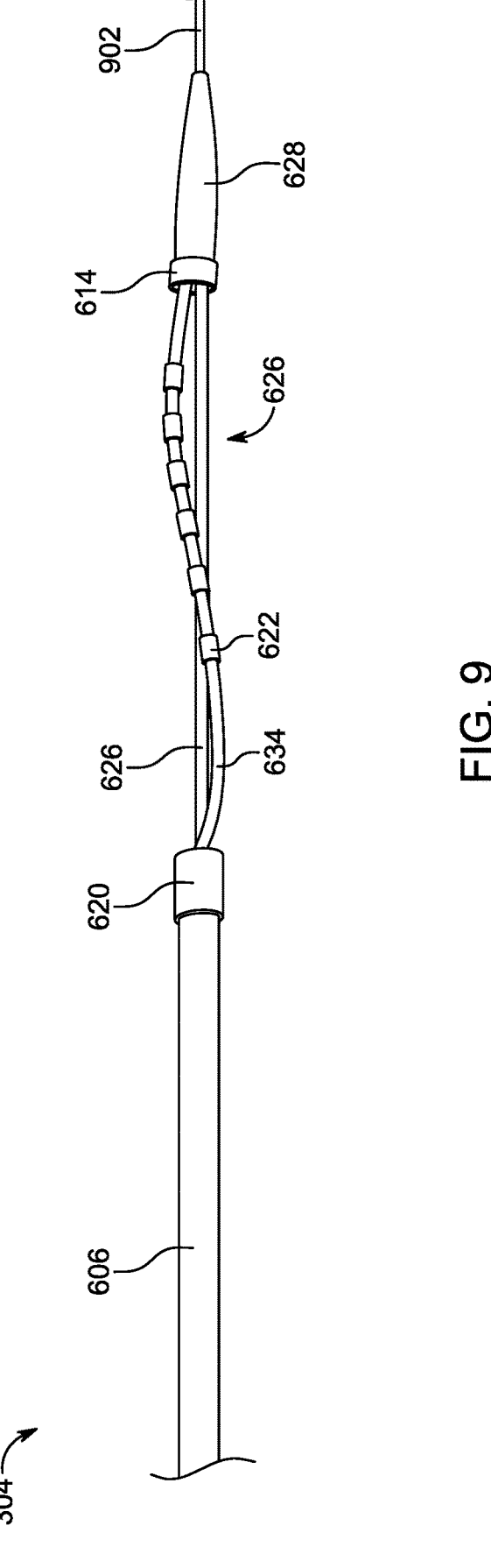
FIG. 9 illustrates a perspective view of a distal portion of the ablation catheter in a partially deployed state, according to an embodiment of the present disclosure.

Referring to FIG. 9, a perspective view of a distal portion of the ablation catheter 304 in a partially deployed state, is disclosed, according to an embodiment.

The second control shaft 626 of the ablation catheter 304 is in linear configuration for advancing the ablation catheter 304 over a guidewire 902. The guidewire 902 may be advanced for an intraluminal advancement when inserted into a femoral vein, and travels to the heart, through the septum separating the right atrium and left atrium (e.g., through a transeptal sheath), and into a pulmonary vein such as the left superior pulmonary vein. The second control shaft 626 is placed in this linear, maximally compact configuration by advancing second control shaft 626, such as by manipulating a control on a handle. The electronic flex cable 634 comprises the ablation and mapping elements 622. The electronic flex cable 634 has a proximal end fixedly attached to the outer shaft 606 via the second ring 620. It can be noted that the second ring 620 may also be referred as a crimp ring. The electronic flex cable 634 distal end is fixedly attached to the second control shaft 626 at a radial location of 90° offset from proximal end attachment, such that the electronic flex cable 634 radially expands as the second control shaft 626 is retracted. The distal end of the second control shaft 626 is covered with the distal tip 628. The first ring 614 is positioned up against the distal tip 628. In one embodiment, the distal tip 628 may be an atraumatic tip with an exit hole (not shown) in communication with the internal guidewire lumen through which guidewire passes.

The present invention provides the ablation catheter 304 for performing targeted tissue ablation on a subject, such as, atrial fibrillation, supra ventricular tachycardia, atrial tachycardia, ventricular tachycardia, ventricular fibrillation, and the like. In one alternate embodiments, the ablation catheter 304 may comprise a tubular body member (not shown) having a proximal end and distal end and preferably a lumen extending therebetween. The ablation catheter 304 is preferably of the type used for performing intracardiac procedures, typically being per subcutaneously introduced and advanced from the femoral vein in a patient's leg. Alternative methods involve percutaneous introduction into the jugular vein of the patient's neck, or other anatomical entry point that can be used to access the target location within the patient. The ablation catheter 304 is preferably introducible through a sheath and preferably is advanceable over a guidewire. The ablation catheter 304 preferably has a steerable tip that allows precise positioning of the distal portion.

The ablation catheter 304 allow generation of lesions of appropriate size and shape to treat conditions involving disorganized electrical conduction (e.g., atrial fibrillation). The created lesions are segmented and localized. The lesions may be linear or curvilinear, circumferential, and partial circumferential, and/or continuous or discontinuous. The ablation catheter 304 are also practical in terms of ease-of-use and limiting risk to the patient, as well as significantly reducing procedure times. The lesions created by the ablation catheter 304 are suitable for inhibiting the propagation of inappropriate electrical impulses in the heart for prevention of reentrant arrhythmias.

In one embodiment, energy to the ablation catheter 304 may be delivered using pulse width modulated drive signals, well known to those of skill in the art. Further, the energy can also be delivered in a closed loop fashion. Such as a system with temperature feedback wherein the temperature modifies the type, frequency and or magnitude of the energy delivered.

In one embodiment, the electrodes or ablation elements may have one or more different shapes. As used herein, the term "proximal and distal energy delivering carrier assemblies" refers to a flexible carrier, on which one or more ablation elements are disposed. The carrier assemblies include one or more carrier arms, as arm segments described above. The carrier assemblies are not limited to, size, or shape, and can be configured to be in expanded and unexpanded or compact states. As used herein, the term "proximal and distal carrier arms" refer to a wire-like shaft capable of interfacing with electrodes and a control shaft. Further, the distal and proximal carrier arms are not limited to any size or measurement.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth here below not be construed as being order-specific unless Such order specificity is expressly stated in the claim.

What is claimed is:

1. An integrated ultrasonic imaging and ablation system comprising:
   an ablation catheter having a longitudinal axis, a proximal end, and a distal end;
   a micro-electromechanical (MEMS) based Piezoelectric Machined Ultrasonic Transducer (pMUT) array comprising a substrate and a plurality of pMUT array elements arranged on the substrate;
   a catheter shaft connected at one end to a handle assembly and at other end to the MEMS based pMUT array;
   a first carrier assembly coupled to the catheter shaft at a proximal end and having a first array of electrodes coupled to a plurality of first carrier arms;
   a second carrier assembly coupled to the catheter shaft at a distal end and having a second array of electrodes coupled to a plurality of second carrier arms, a proximal end of the plurality of second carrier arms being pivotally attached to a distal end of the plurality of first carrier arms; and
   a ring that couples a proximal end of the plurality of second carrier arms to the catheter shaft;
   wherein the MEMS based pMUT array is mounted to the ring.

2. The integrated ultrasonic imaging and ablation system of claim 1, wherein the ablation catheter comprises a steering control unit positioned within the handle assembly, for articulating a distal tip of the ablation catheter and aligning face of the MEMS based pMUT array towards internal views including an anterior position or a posterior position and right or left position of the tissue.

3. The integrated ultrasonic imaging and ablation system of claim 2, wherein the distal tip of the ablation catheter is coated with a material to provide electrical isolation and transmission of ultrasound signals.

4. The integrated ultrasonic imaging and ablation system of claim 1, wherein the ablation catheter is coupled to an imaging device using a dongle, and the dongle is configured to communicate ultrasound transmit pulses and ultrasound receive waveforms between the imaging device and the ablation catheter.

5. The integrated ultrasonic imaging and ablation system of claim 1, wherein each of the plurality of pMUT array elements having transducer cells of multiple diameters, to achieve a wide bandwidth.

6. The integrated ultrasonic imaging and ablation system of claim 1, wherein each of the plurality of pMUT array elements is a linear phased array.

7. The integrated ultrasonic imaging and ablation system of claim 1, wherein each of the plurality of pMUT array elements is a circular array.

8. An integrated ultrasound imaging and ablation system comprising:
   an ablation catheter having a longitudinal axis, a proximal end, and a distal end;
   a catheter shaft connected at one end to a handle assembly and at another end to a ring;
   a first carrier assembly coupled to the catheter shaft and having a first radially expandable array of electrodes coupled to a plurality of first carrier arms; and
   a second carrier assembly coupled to the catheter shaft and having a second radially expandable array of electrodes coupled to a plurality of second carrier arms, a proximal end of the second carrier arms being pivotally attached to a distal end of the plurality of first carrier arms via the ring;

a micro-electromechanical (MEMS) based Piezoelectric Micromachined Ultrasonic Transducer (pMUT) array, wherein the MEMS based pMUT array comprises a substrate and a plurality of MEMS based pMUT array elements arranged on the substrate;

wherein the MEMS based pMUT array is mounted to the ring; and an electronic flex cable connected at one end to the handle assembly and at other end to the MEMS based pMUT array, wherein the electronic flex cable is in communication with at least one signal trace and advances distally inside of the ring, and is further configured to:

direct each of the plurality of MEMS based pMUT array elements, via the at least one signal trace, to transmit and receive, with respect to heart, ultrasound beams;

receive at least one signal from the plurality of MEMS based pMUT array elements based on transmitting and receiving at least one ultrasound beam of the ultrasound beams; and construct at least one image of at least a portion of the heart based on the at least one signal.

9. The integrated ultrasonic imaging and ablation system of claim 8, wherein the ultrasound beams having a bandwidth including a predetermined fundamental mode vibration of each of the plurality of pMUT array elements, such that a single array element transmits and receives multiple fundamental mode vibrations simultaneously.

10. A medical device, comprising:

a catheter shaft comprising an outer shaft, a first control shaft slidingly received by the outer shaft, and a second control shaft slidingly received by the first control shaft;

a first carrier assembly coupled to the first control shaft and having a first radially expandable array of electrodes coupled to a plurality of first carrier arms; and a second carrier assembly rotatably coupled to the second control shaft and having a second radially expandable array of electrodes coupled to a plurality of second carrier arms, the second carrier assembly rotatable about the first carrier assembly;

a ring disposed between the first carrier assembly and the second carrier assembly;

a micro-electromechanical (MEMS) based Piezoelectric Micromachined Ultrasonic Transducer (pMUT) array, wherein the MEMS based pMUT array comprises a substrate and a plurality of MEMS based pMUT array elements arranged on the substrate; and an electronic flex cable connected at one end to a handle assembly and at other end to the MEMS based pMUT array, wherein a distal end of the electronic flex cable is connected at a radial location on the catheter shaft that is offset from where a proximal end of the electronic flex cable is connected on the catheter shaft; and wherein the MEMS based pMUT array is mounted to the ring; and the electronic flex cable distally advances inside of the ring.

11. The medical device of claim 10, wherein the first radially expandable array of electrodes having a series of longitudinally spaced electrodes.

12. The medical device of claim 10, further comprising a mapping element coupled to the first carrier assembly.

13. The medical device of claim 12, wherein the mapping element is distal to the first radially expandable array of electrodes.

14. The medical device of claim 10, wherein the catheter shaft defines a guidewire lumen.

15. The medical device of claim 12, wherein the offset from where the proximal end of the electronic flex cable is connected to the catheter shaft is about 90°.

* * * * *